US00PP15932P2

(12) United States Plant Patent
Stemkens

(10) Patent No.: US PP15,932 P2
(45) Date of Patent: Aug. 30, 2005

(54) ***VERBENA×HYBRIDA* PLANT NAMED 'VERENA'**

(50) Latin Name: *Verbena×hybrida*
Varietal Denomination: Verena

(75) Inventor: Henricus Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 149 days.

(21) Appl. No.: 10/795,614

(22) Filed: Mar. 8, 2004

(51) Int. Cl.[7] ..... A01H 5/00
(52) U.S. Cl. ..... Plt./308
(58) Field of Search ..... Plt./308

(56) References Cited

PUBLICATIONS www.Kemsnursery.com.*
UPOVROM 2004/02.*

* cited by examiner

*Primary Examiner*—Anne Marie Grunberg
*Assistant Examiner*—Annette H Para
(74) *Attorney, Agent, or Firm*—Edouard G. Lebel

(57) ABSTRACT

A new and distinct variety of *Verbena* plant named 'Verena' particularly distingushed by its deeppink flower, incised leaves, early flowering and a spreading habit that is first semi-erect and later spreading.

1 Drawing Sheet

Latin name of the genus and species of the plant claimed: *Verbena×hybrida*.
Varietal denomination: 'Verena'.

BACKGROUND OF THE NEW PLANT

The present invention comprises a new distinct cultivar of *Verbena*, botanically known as *Verbena×hybrida*. The new cultivar is propagated from cuttings resulting from the cross of 'W720' and 'T593'. 'W720' is a rose flowering *Verbena* having a spreading habit. 'W720' is not commercially available and is not known by any synonyms. 'T593' is a scarlet flowering *Verbena* having a semi-erect habit. 'T593' is not commercially available and is not known by any synonyms. Neither 'W720' or 'T593' has been patented. As a result of this cross the present cultivar was created in 1999 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new *Verbena* plant is an annual in most climatical zones in the US, only in zones 9 and 10 it is a perennial plant.

DESCRIPTION OF THE DRAWING

This new *Verbena* plant is illustrated by the accompanying photographic drawing which shows blooms, buds and foliage of the plant in full colour, the colour shown being as true as can be reasonably obtained by conventional photographic procedures.

DESCRIPTION OF THE NEW CULTIVAR

The following detailed descriptions set forth the distinctive characteristics of this new *Verbena*. The data which defines these characteristics were collected from asexual reproductions carried out in Enkhuizen, Netherlands. The plant history was taken on 14 weeks old plants, blossomed under natural light in a greenhouse. Colour readings were taken in the greenhouse under ambient light. Colour references are primarily to The R.H.S. Colour Chart of The Royal Horticultural Society of London.

Specification of differences with parents and most resembling variety

| Character | 'Verena' | 'W720' | 'T593' | 'Temari coral rose' |
|---|---|---|---|---|
| Flowercolor | deeppink | rose | scarlet | coral rose |
| Earliness | early | very early | late | late |
| Seedset | no | no | much | abundant |
| Leave incision | double incised | double incised | no incisions | no incisions |

The Plant

Classification — Botanical: *Verbena×hybrida*.
Parentage:
*Female parent.*—A seedling named 'W720' is one of our seedlings from our W-generation of plants bred in 1994.
*Pollen parent.*—A seedling named 'T593' is one of our seedlings from our T-generation of plants bred in 1991.
Growth habit: Semi-erect later spreading.
Plant height: 18–26 cm.
Spreading area of plant: 32–60 cm.
Growth rate: Hanging and vigorous.
Strength: Resistant to hot and cold weather.
Branching character: Freely branching and lateral branching at every node.
Blooming period: From April till November.

The Stem

Diameter: 2 to 2.5 mm.
Shape: Tetragonal.
Anthocyan pigmentation: Present.

Colour: 141C.
*Length of internode.*—25 to 35 mm, depending on the light where the plant is propagated.
Pubescence: Pubescence is present.

The Foliage

Phyllotaxis: Opposite.
Shape of blade: Broadly ovate.
Texture:
*Upper side.*—Smooth.
*Lower side.*—Smooth.
Venation: Pinnate.
Leaf margin: Laciniate.
Leaf base: Hastate.
Leaf apex: Acute.
Length: 16 to 25 mm.
Width: 14 to 22 mm.
Depth of incision: 8 to 10 mm.
Number of incisions: 2 to 5 per leaf.
Colour:
*Upper side.*—141B.
*Lower side.*—138B.
Pubescence: Some pubescence is present.
Length of leaf stem: 8 to 12 mm.
Petiole surface structure: Slightly pubescent.

The Bud

Peduncle length: 20 to 30 mm, depending on season.
Size:
*Diameter.*—2 mm.
*Length.*—8 to 10 mm.
Shape: Elongated and ovate.
Colour: 137C.
Sepals:
*Colour.*—138C.
*Form.*—Upright.
*Number.*—5, fused.
*Size.*—5 mm.
*Shape.*—Elongated.

The Flower

Facing direction: Upward.
Outward curvature of petal: Slightly curved.
Diameter: 14 to 18 mm.
Height: 14 to 16 mm.
Borne: In a cluster.
Form: Salverform; sessile on terminal spikes.
Cluster: Spike.
Colour: 37A.
Eye: A very small (1 mm) greenish eye (155B) is present. Typically three out of the five petals exhibit this greenish coloration.
Overlapping of petals: Separate.
No. of petals: Gamopetalous, 5lobed.
Shape of the petals: Each petal is heart shaped at the apex and grown together at the base.
Petal margin: Entire.
Petal surface texture: Smooth.
Size of the petal:
*Length.*—4 to 6 mm.
*Width.*—5 to 8 mm.
Spike:
*Length.*—32 to 40 mm.
*Diameter.*—35 to 45 mm.
Calyx length: 8 to 10 mm.
Anthocyan pigmentation of calyx limb: Absent.
Color of the calyx: 137A.
No. of flowers per spike: 25 to 45.
Fragrance: A very light rosy fragrance.
Lastingness of the bloom: New florets continue to open in one spike over a period of 14 days.

Reproductive Organs

Androecium:
*Stamens quantity.*—4.
*Anther shape.*—Ovoid.
*Anther length.*—1 mm.
*Anther color.*—144C.
*Pollen amount.*—No pollen.
Gynoecium.
*Pistils quantity.*—1.
*Pistil length.*—1.8 to 2.2 cm.
*Stigma shape.*—Bi-lobed.
*Stigma color.*—144C.
*Style length.*—1.6 cm.
*Style color.*—144D.
*Ovary color.*—144C.
No seedset is observed.

Roots

Type of roots: Fibrous. Roots start to grow on every part of the stem that contacts the soil, so not only at the nodes.
Description of roots: Fibrous, fleshy and white.
Rooting habit: Freely branching, dense.

Physiological and Ecological Characteristics

Good tolerance to heat and cold. Strong resistance to pests and diseases, particularly powdery mildew.

What is claimed is:

1. A new and distinct variety of *Verbena* plant, substantially as herein illustrated and described, characterized particularly as to novelty by deeppink flowers, which appear earlier on the plant, by incised darkgreen leaves and a growing habit that is first semi-erect and later spreading.

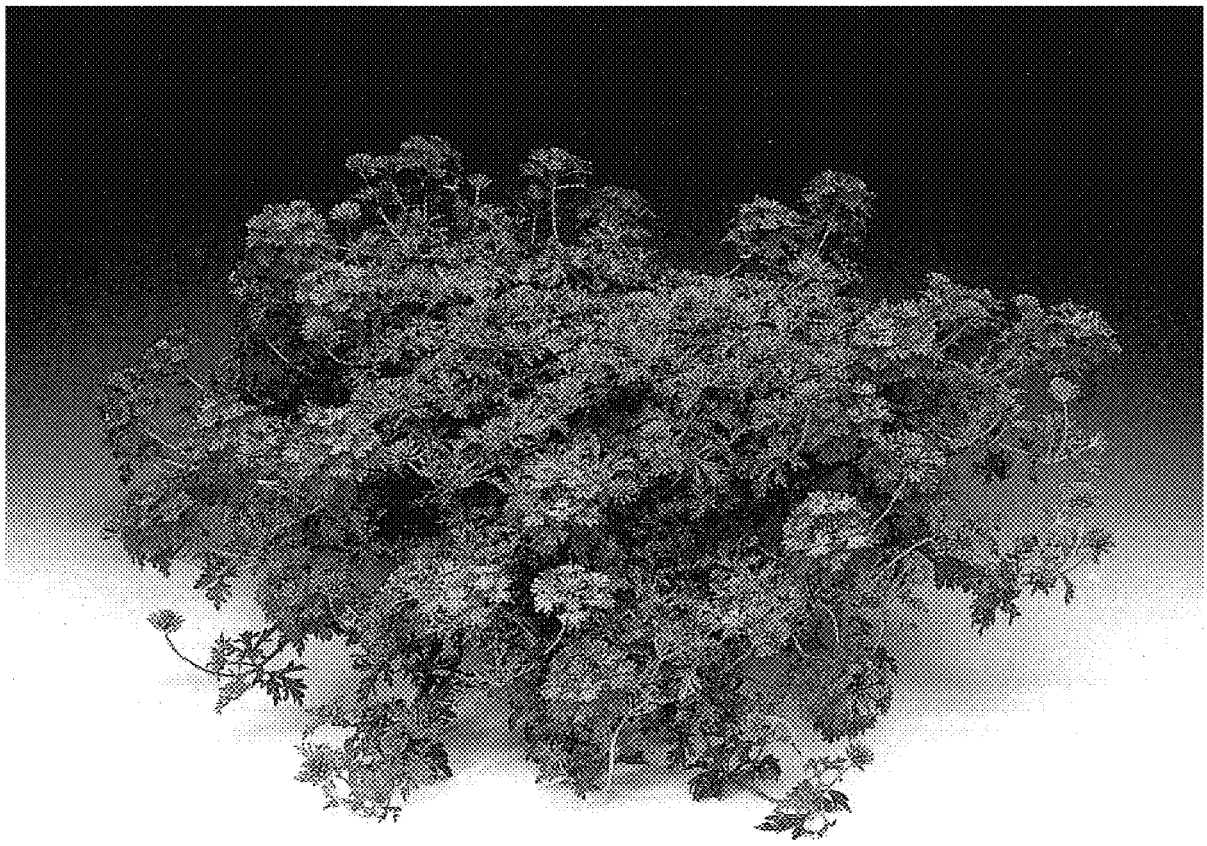

* * * * *